United States Patent
Theobald et al.

(10) Patent No.: US 9,675,361 B2
(45) Date of Patent: Jun. 13, 2017

(54) COIL OCCLUSION DEVICE

(71) Applicant: Cook Medical Technologies LLC, Bloomington, IN (US)

(72) Inventors: Elizabeth Theobald, Bloomington, IN (US); Andrew Conder, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 236 days.

(21) Appl. No.: 14/634,134

(22) Filed: Feb. 27, 2015

(65) Prior Publication Data

US 2015/0245843 A1    Sep. 3, 2015

Related U.S. Application Data

(60) Provisional application No. 61/945,864, filed on Feb. 28, 2014.

(51) Int. Cl.
*A61M 29/00* (2006.01)
*A61B 17/12* (2006.01)

(52) U.S. Cl.
CPC ...... *A61B 17/1215* (2013.01); *A61B 17/1214* (2013.01); *A61B 17/12031* (2013.01); *A61B 17/12109* (2013.01)

(58) Field of Classification Search
CPC .......... A61B 17/1215; A61B 17/12109; A61B 17/1214; A61B 17/12031
See application file for complete search history.

(56) References Cited

U.S. PATENT DOCUMENTS

| | | | |
|---|---|---|---|
| 5,556,426 A | 9/1996 | Popadiuk et al. | |
| 5,582,619 A * | 12/1996 | Ken | A61B 17/12022 606/108 |
| 5,628,782 A | 5/1997 | Myers et al. | |
| 5,690,671 A | 11/1997 | McGurk et al. | |
| 5,718,159 A | 2/1998 | Thompson | |
| 5,733,294 A | 3/1998 | Forber et al. | |
| 5,797,953 A | 8/1998 | Tekulve | |
| 5,976,192 A | 11/1999 | McIntyre et al. | |
| 6,019,786 A | 2/2000 | Thompson | |
| 7,115,220 B2 | 10/2006 | Dubson et al. | |
| 7,166,122 B2 * | 1/2007 | Aganon | A61B 17/12022 606/200 |
| 7,582,104 B2 | 9/2009 | Corcoran et al. | |
| 7,998,188 B2 | 8/2011 | Zilla et al. | |
| 8,007,509 B2 | 8/2011 | Buiser et al. | |
| 8,337,650 B2 | 12/2012 | Edwin et al. | |
| 8,377,110 B2 | 2/2013 | Douglas et al. | |
| 8,389,088 B2 | 3/2013 | Hood et al. | |
| 2001/0012949 A1 | 8/2001 | Forber | |
| 2002/0016597 A1 | 2/2002 | Dwyer et al. | |

(Continued)

*Primary Examiner* — Todd J Scherbel
*Assistant Examiner* — Son Dang
(74) *Attorney, Agent, or Firm* — Brinks Gilson & Lione

(57) ABSTRACT

An occlusion device comprising a plurality of inner coils and a plurality of outer coils is described. When the device is deployed to a body vessel or a body cavity, it expands radially due to the material from which the outer coils are made. The inner coils function to occlude the vessel while the outer coils provide support. The device can be capped at both ends or may have a free distal end. A method of deploying the device is also provided.

19 Claims, 7 Drawing Sheets

(56) References Cited

U.S. PATENT DOCUMENTS

| | | |
|---|---|---|
| 2002/0193825 A1 | 12/2002 | McGuckin, Jr. et al. |
| 2003/0199919 A1 | 10/2003 | Palmer et al. |
| 2005/0283220 A1 | 12/2005 | Gobran et al. |
| 2006/0079926 A1* | 4/2006 | Desai ............... A61B 17/12022 606/200 |
| 2007/0060994 A1 | 3/2007 | Gobran et al. |
| 2007/0083226 A1 | 4/2007 | Buiser et al. |
| 2008/0208325 A1 | 8/2008 | Helmus et al. |
| 2009/0024205 A1 | 1/2009 | Hebert et al. |
| 2010/0030321 A1 | 2/2010 | Mach |
| 2011/0288628 A1 | 11/2011 | Noesner et al. |
| 2012/0310319 A1 | 12/2012 | Tieu et al. |
| 2013/0085518 A1 | 4/2013 | Trommeter et al. |
| 2013/0112070 A1 | 5/2013 | Mach |

\* cited by examiner

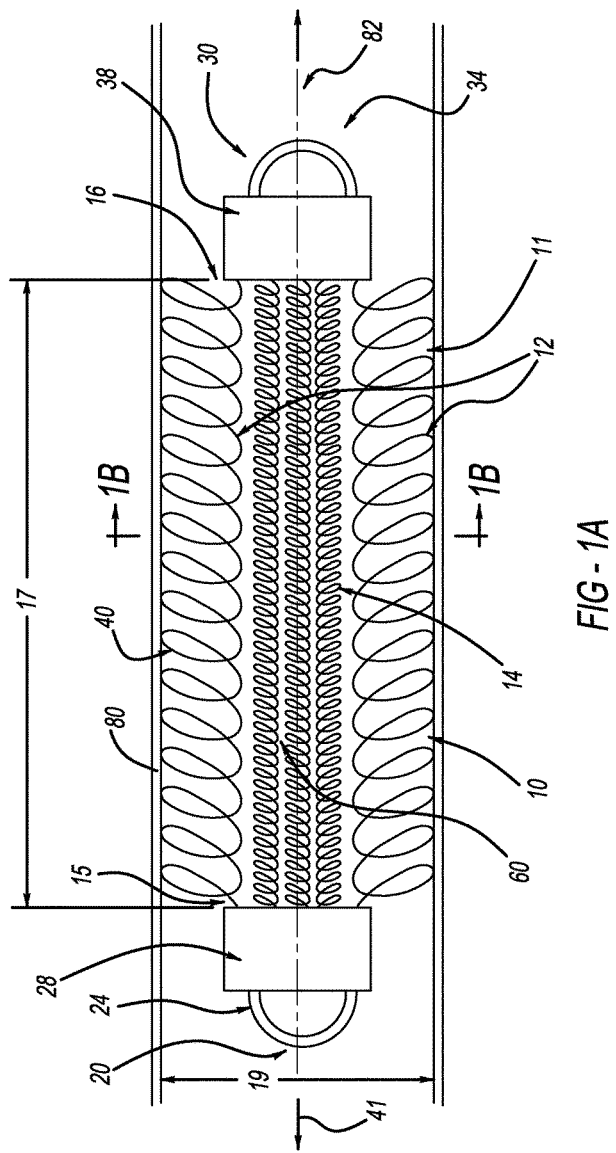

COIL OCCLUSION DEVICE

CROSS-REFERENCE TO RELATED APPLICATIONS

This application claims priority to U.S. Provisional Patent Application Ser. No. 61/945,864, filed Feb. 28, 2014, entitled "COIL OCCLUSION DEVICE", the entire contents of which are incorporated herein by reference.

BACKGROUND OF THE INVENTION

Field of Invention

The present invention relates to medical devices. More particularly, the invention relates to an occlusion device for occluding a lumen of a body vessel.

Background

Vascular occlusion devices are surgical implants that are placed within the vascular system of a patient. There are a number of reasons why it may be desirable to occlude a vessel. For example, the site of a stroke or other vascular accident can be treated by placing an occlusion device proximal of the site to block the flow of blood to the site, thereby alleviating leakage at the site. An aneurysm can be treated by the introduction of an occlusion device through the neck of the aneurysm. Tumours can be treated by occluding the flow of blood to a targeted site of interest.

Several known occlusion devices include a coiled apparatus which is capable of being deployed into a body vessel or body cavity. In some cases, occlusion can be achieved with the deposition of a single coil. In other cases, multiple coils must be deployed to the occlusion site, prolonging the procedure. Furthermore, it cannot always be predicted how many coils may need to be introduced to a particular site. In some cases, the coils are made of expensive materials, such as platinum, thereby increasing both the cost and complexity of such procedures.

While these occlusion devices can provide effective occlusion, there is a need for a single device that can be deployed to the body cavity or body vessel to be occluded to affect occlusion in a single step.

BRIEF SUMMARY OF THE INVENTION

One embodiment of an occlusion device, having a longitudinal axis, generally includes a plurality of outer coiled elements having a first proximal end extending distally to a first distal end, each outer coiled element having a first diameter and a first length dimension. In this case, the first length dimension may be substantially parallel to the longitudinal axis. The plurality of outer coiled elements may define a device body having a proximal device end extending distally to a distal device end and an interior device lumen disposed therethrough. The device body may include a body outer surface disposed about the interior device lumen wherein each outer coiled element is disposed about the body outer surface. The device body may further have a device midpoint disposed substantially halfway between the proximal device end and the distal device end.

The occlusion device further includes a plurality of inner coiled elements disposed in the interior device lumen, each inner coiled element having a second proximal end extending distally to a second distal end, each inner coiled element having a second length dimension and a second diameter, the second diameter may be less than the first diameter of any of the plurality of outer coiled elements.

The occlusion device further has a proximal cap disposed at the proximal device end, the proximal cap comprising a first interior portion and a first exterior portion, the first proximal ends of the outer coiled elements and the second proximal ends of the inner coiled elements being fixed within the first interior portion of the proximal cap.

In another embodiment, an occlusion device includes an outer coiled element, similar to the outer coiled elements discussed above. The outer coiled element may have a first proximal end extending distally to a first distal end, the outer coiled element having a first diameter and a first length dimension. The first length dimension may be substantially parallel to the longitudinal axis, the outer coiled element comprising a series of first coil loops Each first coil loop may have a radius, each first coil loop being spaced substantially equidistant from the first coil loop proximal to and distal to it. The radius of each first coil loop may be larger than that of the first coil loop proximal to it. The first coil loops may define a device body having a proximal device end extending distally to a distal device end and an interior device lumen disposed therethrough, the device body comprising a body outer surface disposed about the interior device lumen wherein each outer coiled element is disposed about the body outer surface.

The occlusion device may further include a plurality of inner coiled elements disposed in the interior device lumen, each inner coiled element having a second proximal end extending distally to a second distal end, each inner coiled element having a second length dimension and a second diameter, the second diameter being less than the first diameter of the outer coiled element. The device may also include a proximal cap disposed at the proximal device end, the proximal cap comprising a first interior portion and a first exterior portion, the first proximal end of the outer coiled element and the second proximal ends of the inner coiled elements being fixed within the first interior portion of the proximal cap.

In another embodiment, the present invention provides a method of delivering an occlusion device to a body vessel or a body cavity. The method includes providing a delivery sheath having an interior lumen and an occlusion device, the occlusion device as discussed herein having a plurality of outer coiled elements, a plurality of inner coiled elements, and a proximal cap.

The occlusion device may further include a constrained configuration wherein the device body has a constrained length and a constrained diameter and an unconstrained configuration wherein the device body has an unconstrained length and an unconstrained diameter. The constrained length may be greater than the unconstrained length. The constrained diameter may be smaller than the unconstrained diameter.

The method further includes disposing the device in its constrained configuration within the interior lumen of the delivery sheath, and delivering the device percutaneously to a body vessel using the delivery sheath.

Further objects, features, and advantages of the present invention will become apparent from consideration of the following description and the appended claims when taken in connection with the accompanying drawings.

BRIEF DESCRIPTION OF THE DRAWINGS

FIG. 1A is side view of an occlusion device inside a delivery catheter in accordance with the teachings of the present invention;

DETAILED DESCRIPTION OF THE INVENTION

Figure 1B:
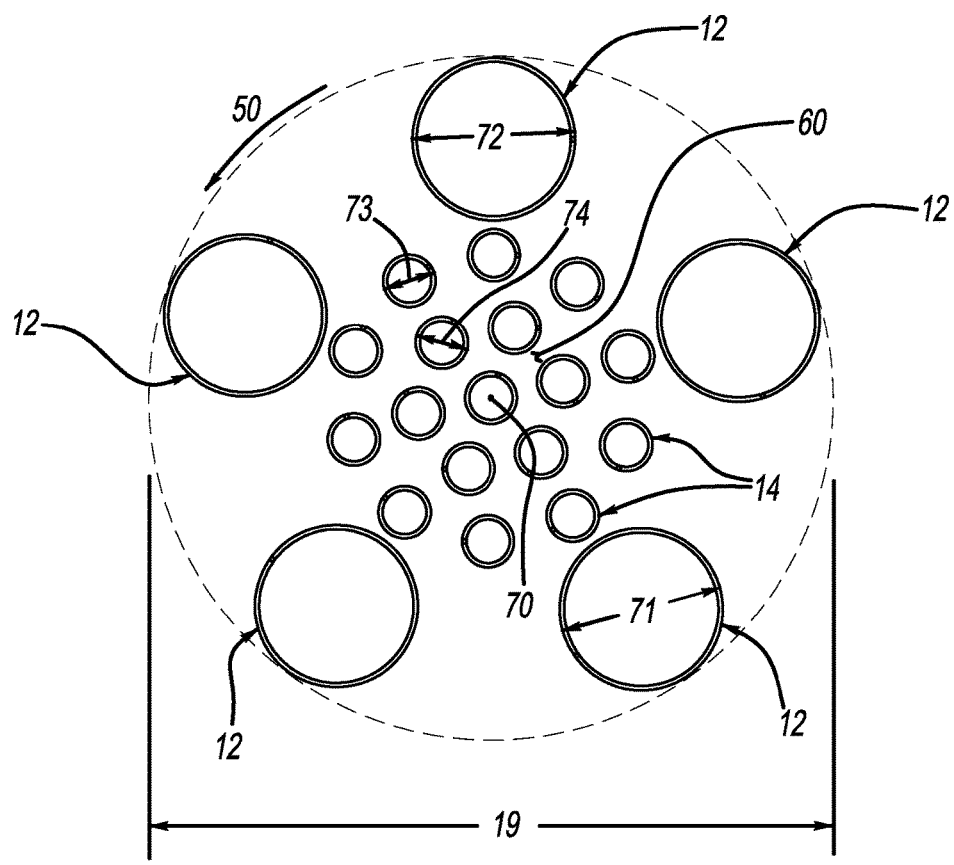
FIG. 1B is a cross sectional view of the occlusion device of FIG. 1A.

The description that follows is not intended to limit the scope of the invention in any manner, but rather serves to enable those skilled in the art to make and use the invention.

In this description, when referring to a device, an introducer, or deployment assembly, the term distal is used to refer to an end of a component which in use is furthest from the physician during the medical procedure, including within a patient. The term proximal is used to refer to an end of a component closest to the physician and in practice in or adjacent an external manipulation part of the deployment or treatment apparatus. Similarly, when referring to an implant such as an occlusion device the term distal is used to refer to an end of the device which in use is furthest from the physician during the medical procedure and the term proximal is used to refer to an end of the device which is closest to the physician during the medical procedure.

The terms "substantially" or "about" used herein with reference to a quantity includes variations in the recited quantity that are equivalent to the quantity recited, such as an amount that is equivalent to the quantity recited for an intended purpose or function.

The present disclosure generally provides an occlusion device which can be used with any suitable occlusion device delivery system by a physician to deliver an occlusion device into a body vessel or a cavity of a patient.

Referring to FIG. 1A, one embodiment of an occlusion device 10 is depicted inside a delivery catheter 80. The occlusion device 10 generally comprises a plurality of outer coils or outer coiled elements 12 and a plurality of inner coils or inner coiled elements 14. The outer coiled elements may have a first length dimension substantially parallel to the longitudinal axis.

These outer coiled elements may define a device body having a device proximal end 20 extending distally to a distal device end 30. The device body may include a body outer surface and each outer coiled element is disposed about the body outer surface.

In this embodiment, there is a proximal cap 28 located at the proximal end of the device and a distal cap 38 at the device distal end. In this embodiment, proximal loop or engagement loop 24 is attached to an outer surface of proximal cap 28, and distal loop 34 is attached to an outer surface of proximal cap 28. As depicted, this occlusion device 10 is positioned within catheter lumen 82 of delivery catheter 80.

The occlusion device 10 is depicted in a first configuration 11. When the device 10 is in first configuration 11, it has a first length 17 and defines a first device diameter 19. The device is configured to expand radially in order to fill the vessel, cavity, or delivery apparatus in which it is placed, therefore making device diameter 19 equal to the diameter of the catheter 80. The device diameter 19 can also be considered a height dimension for the device. Substantially halfway along the first length 17, between the proximal end 20 and the distal end 30, is device midpoint 40, which falls along a longitudinal axis 41. The occlusion device 10 can be used in a number of contexts: for occlusion of a blood vessel, for instance, or to fill an aneurysm.

The plurality of outer coils 12 are disposed about and comprise a device circumference or body outer surface 50 of the device 10. The outer coils 12 also define a device lumen 60 interior to the outer coils 12. The plurality of inner coils 14 are located within the device lumen 60. The longitudinal axis 41 runs through the device lumen 60. Optionally, the first length 17 can be measured along the longitudinal axis 41. A circle can be drawn along a portion of device circumference 50 using device midpoint 40 as its center to define a central lumen plane.

In certain embodiments, the proximal end 20 and the distal end 30 of device 10 may be indistinguishable from one another. If there is no distinguishing characteristic incorporated in the device 10 which differentiates proximal end 20 from distal end 30, the device may be reversible; that is, either end may be termed the proximal or the distal end. In other embodiments, the device 10 may have a distinct proximal end 20 as compared to the distal end 30. For instance, a radiopaque marker may be incorporated into the device at a certain point, defining polarity of the device. For example, the optional distal loop 34 may be left off. The single-looped device may then have a proximal end 20 with a proximal cap 28 having proximal loop 24 thereon, and distal end 30 with a cap 38 that lacks a loop.

With respect to FIG. 1B, a cross sectional view along line 1B of the device of FIG. 1A is shown. The outer coiled elements 12 are shown disposed about and defining the device circumference 50 and forming the outer limit of device lumen 60. At the center of device lumen 60 is device center 70, which is coincident with the longitudinal axis 41 of the device as it passes through the space occupied by the device 10. In the embodiment depicted, the device 10 comprises five outer coils 12. However, other numbers of outer coils are possible. A device may have as few as three outer coils 12, but may also have four, five, six, seven, eight, nine, ten, or more than ten outer coils 12. In some embodiments, the outer coils 12 are evenly spaced about the device center 70 along device circumference 50. In other embodiments, they may be unevenly spaced.

As depicted in FIG. 1B, one of the outer coils 12 has a first outer coil diameter 71 while another has second outer coil diameter 72. In one embodiment, the first outer coil diameter 71 is substantially the same as second outer coil diameter 72. In another embodiment, first outer coil diameter 71 is substantially larger than second outer coil diameter 72. It may be preferable in certain embodiments to have outer coils 12 that all have the same diameters. In other embodiments, it may be preferable to have one or more of the plurality of outer coils 12 that have different diameters from the other outer coils 12.

The plurality of inner coils 14 is shown in the lumen 60 of device 10. The number of inner coils 14 can be varied based on the properties of the coils selected for use as inner coils and based on the overall diameter of the device lumen 60. In some embodiments, five or more inner coils 14 will be employed; in other embodiments, ten or more inner coils 14 will be included; in still other embodiments, twelve, fifteen, twenty, or more inner coils 14 will be included in the lumen 60 of device 10.

As depicted in FIG. 1B, one of the outer coils 14 has a first inner coil diameter 73 while another has second inner coil diameter 74. In one embodiment, the first inner coil diameter 73 is substantially the same as second inner coil diameter 74. In another embodiment, first inner coil diameter 73 is substantially larger than second inner coil diameter 74. It may be preferable in certain embodiments to have outer coils 14 that all have the same diameters. In other embodiments, it may be preferable to have one or more of the plurality of inner coils 14 that have different diameters from the other inner coils 14.

Figure 1C:
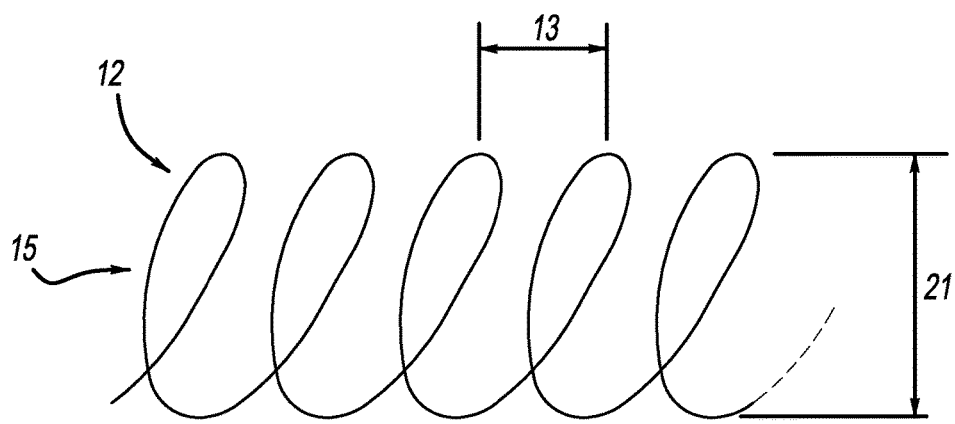
FIG. 1C is a side view of an outer coil of the device of FIG. 1A.

Referring to FIG. 1C, an individual outer coil 12 is depicted. The outer coil 12 comprises a number of windings from the first proximal end 15 to the distal end. In one embodiment, the first winding lengths 13 between equivalent points on consecutive windings of the coil are equal along the entire length of the coil. The windings can extend from the proximal device end 20 to the distal device end. The outer coil 12 also has a first coil height 21, which is defined as the diameter of the largest coil winding. In certain embodiments, the heights of each coil winding segment are all equal to one another along the length of the coil. In other embodiments, the coil winding segment at the proximal end 15 of the coil may have a height dimension which is substantially smaller than the one distal to it, and the next coil winding segment may be have a substantially larger height to that coil winding segment. This would result in a tapered coil with the largest coil winding segment height at its distal end, bearing a resemblance in shape for instance to the Cook TORNADO embolization coil or a coil of the type described in U.S. Pat. No. 5,797,953, which incorporated herein in its entirety by reference.

The outer coils 12 can in some embodiments have a greater stiffness than the inner coiled elements 14. In one embodiment, the outer coils 12 are made of a metal alloy with high stiffness, such as Inconel or elgiloy. Inconels are alloys of varying composition that are primarily nickel alloyed with a smaller amount of chromium and other metals. Inconel alloys are oxidation and corrosion resistant materials well suited for medical device applications. Compressing an Inconel assembly such as outer coils 12 in the first configuration 11 of device 10 will create a tension force in the radial direction which will be alleviated when the coil is released into the body vessel and will serve to accelerate ejection of the device from the delivery catheter 80. Inconel also has an additional advantage of good radiopacity so that placement of devices incorporating it can be visualized.

Elgiloy is a cobalt-chromium-nickel alloy that exhibits high strength and low corrosion, making it suitable for inclusion in a medical device. Of course, any metal with suitable stiffness and biocompatibility, such as stainless steel, may be used for the outer coils 12. In one embodiment, the outer coils are instead made of a shape-memory alloy such as nitinol.

Figure 1D:
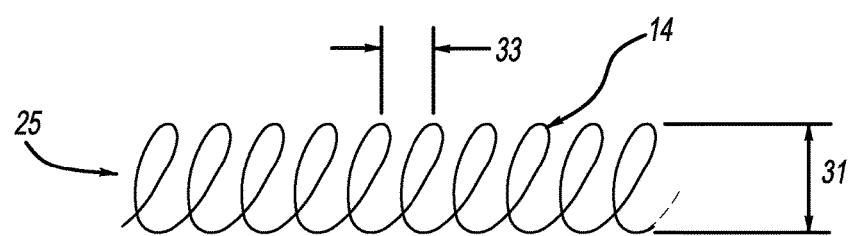
FIG. 1D is a side view of and inner coil of the device of FIG. 1A.

Referring now to FIG. 1D, a single inner coil 14 is depicted. The inner coil 14 comprises a number of windings from the first proximal end 25 to the distal end. In one embodiment, the second winding lengths 33 between equivalent points on consecutive windings of the coil are equal along the entire length of the coil. The windings can extend from the proximal device end 20 to the distal device end. In some embodiments, some individual inner coils 14 can have a shorter length than the outer coils 12. The inner coil 14 also has a second coil height 21, which is defined as the diameter of the largest coil winding. In certain embodiments, the heights of each coil winding segment are all equal to one another along the length of the coil.

In contrast with the relatively stiff outer coils 12, the inner coils 14 may in some embodiments be relatively soft, flexible, or pliable. In one embodiment, the inner coils 14 are made of platinum. Platinum has been used in numerous embolization coils and occlusion devices, such as Cook NESTER coils and platinum Cook TORNADO microcoils. Like platinum, palladium is another metal which is well suited for making inner coils 14. Both platinum and palladium are soft, unreactive, and capable of conforming to the anatomy of a patient. In cases where the device 10 will be deployed to body vessels or body cavities of irregular shape, the flexibility of the inner coils 14 will ease stress on the device and hasten the deployment process. In other embodiments, the inner coils 14 can be made of other metals, or of nonmetals such as polymers having the appropriate properties for proper occlusion.

Referring again to FIG. 1A, the plurality of outer coils 12 are fixed at the first proximal ends 15 inside of an interior lumen or first interior portion of proximal cap 28 or first interior portion. Likewise, the plurality of inner coils 14 are fixed at their second proximal ends 25 inside of an interior lumen of proximal cap 28. Likewise, the distal ends of the outer coils 12 and the inner coils 14 are fixed within a lumen of distal cap 38 or second interior portion. The ends of the coils can be fixed in any manner suitable to maintaining the integrity of the device during delivery and after deployment. For instance, the inner surface or lumen of a cap may have a post or loop which the ends of the coils can be wrapped around and secured. In another embodiment, the ends of the coils may be welded to the inner surface of the cap.

In another embodiment, the proximal or distal cap, or both, may be solid. In such a case, the coils would be secured to an outer surface of the caps rather than an inner surface. In another embodiment, some of the inner coils may not be long enough to contact both the proximal and the distal cap. In such a case, only one end of such coils would be attached to a cap portion of the occlusion device 10.

Figure 2:
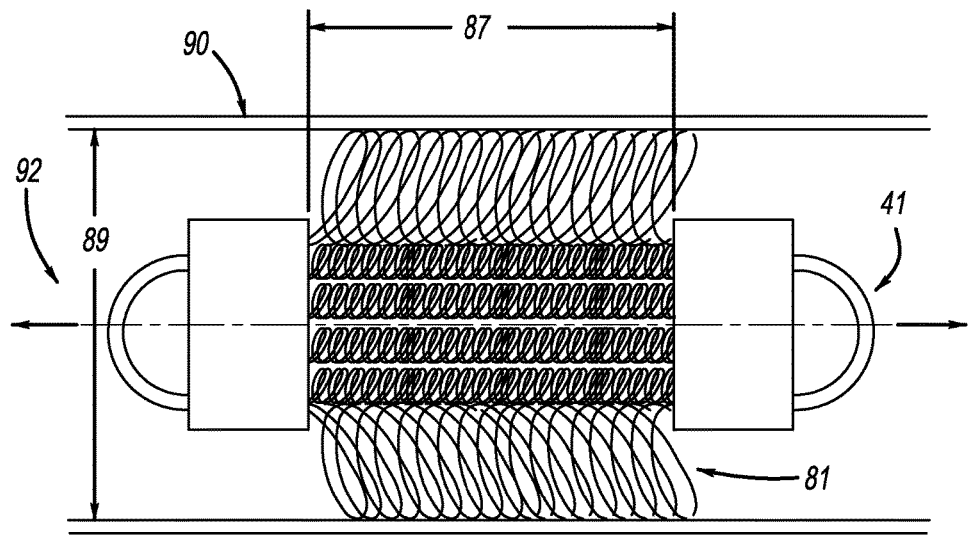
FIG. 2 is a side view of the occlusion device of FIG. 1A when deployed in a body vessel.

Referring now to FIG. 2, the device of FIG. 1A is depicted deployed in lumen 92 of a body vessel 90 rather than a catheter. The device as deployed is in its second configuration 81, or deployed configuration. Having been transferred from a catheter of a smaller diameter to a body vessel 90 with a larger diameter, the device has expanded radially and the outer coils 12 have contracted as a result. Stated another way, the second device diameter 89 is greater than the first device diameter 19, whereas the second device length 87 is smaller or less than the first device length 17. The stiffness of the coils creates a lengthening and contracting phenomenon similar to a spring, where the contracted state is favored. Packing in the delivery apparatus causes lengthening and stretching of the outer coils 12 functioning similar to a spring, and release into a vessel lumen or cavity of a greater diameter causes a shortening of the distance 13 between windings of the coils and a degree of radial expansion.

Figure 3:
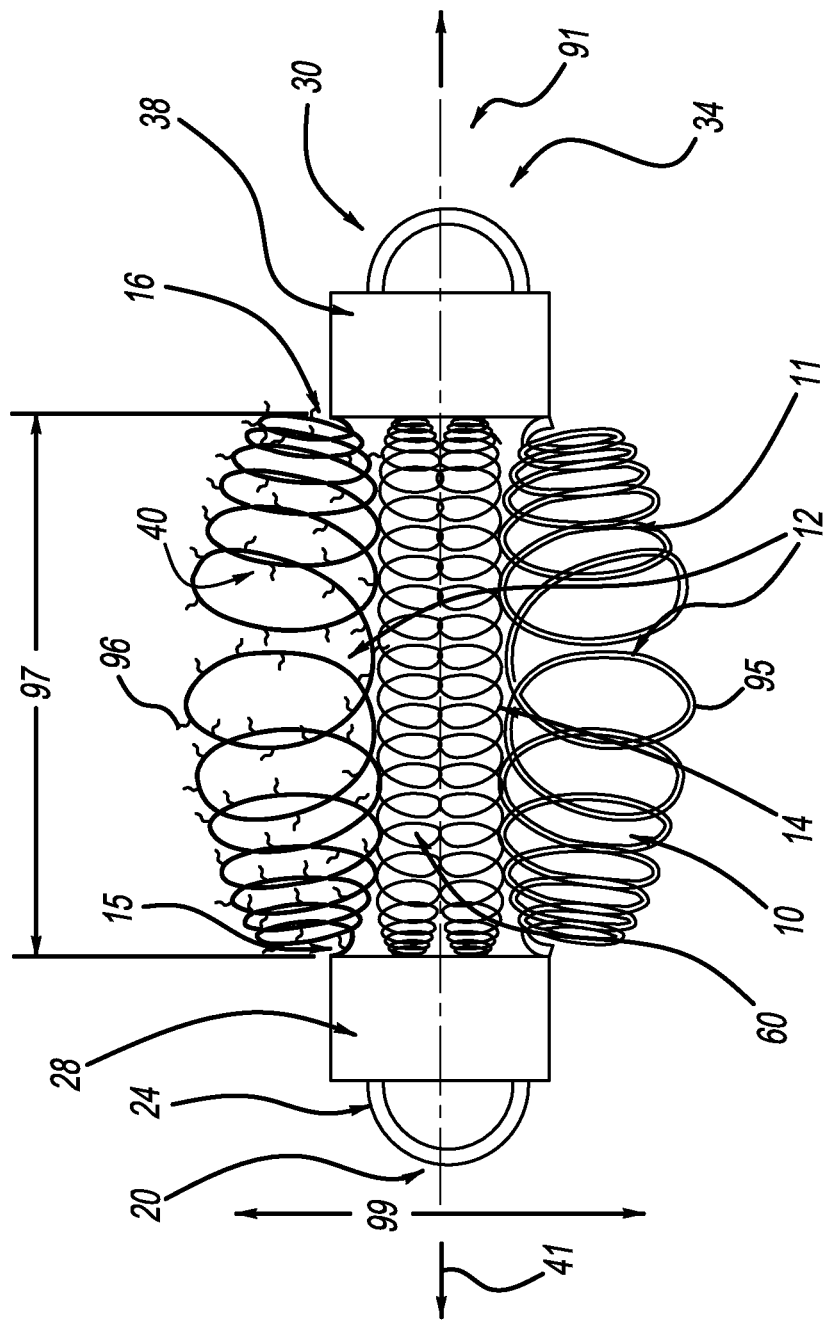
FIG. 3 is a side view of the occlusion device of FIG. 1A in its unconstrained configuration.

Turning now to FIG. 3, a third configuration 91 is depicted. In this configuration, the device is not constrained radially by either a body vessel or a catheter; rather, it is depicted in a state in which it is not being acted upon by outside forces. In this third configuration 91, the outer coils 12 arc outward, away from the longitudinal axis 41 that runs through the device. The device 10 has a third device length 97, which is shorter than device length 17 when the device is in its first, configuration 11 as depicted in FIG. 1A.

In the third configuration 91, a third device diameter dimension 99 is observed, which represents the maximum diameter of the device 10. In some embodiments, this is the diameter of the central lumen plane which is defined by the circle drawn along a device circumference 50 using the device midpoint 40 as the center of the circle. The diameter of the device at any given point in such an embodiment will decrease from the device midpoint 40 along the longitudinal axis 41 either toward the proximal end 20 or the distal end 30. In its unconstrained state, a device in third configuration 91 may have the shape of an oblate spheroid.

In certain embodiments, the occlusion device may optionally comprise thrombogenic material in order to encourage further occlusion. Thrombogenic fibers 96 are depicted on an outer coil 12 of the device. Suitable synthetic fibers include polyethylene terephthalate (DACRON), polyesters, polyamides (nylons), polyglycolic acid, polylactic acid, and the like. Other synthetic polymers having a lesser degree of thrombogenicity include fluorocarbons (Teflon) and polyaramids (Kevlar). Natural fibers such as silk and cotton are also suitable materials. The fibers may be attached to a portion of the device in any acceptable way. As shown in FIG. 3, individual fibrous elements 96 are dispersed about one of the outer coils 12 at various intervals, whereas elongated fibrous element 95 is wrapped, wound, or woven about another outer coil 12 across a greater length of the coil. The outer coiled elements may have at least one portion with thrombogenic fibers.

Thrombogenic fibers or coatings may be applied to some of the outer coils 12, all of the outer coils 12, or portions of the outer coils. Such fibers or coatings may also be applied to the inner coils 14 or portions thereof. Both outer coils and inner coils may be coated or have thrombogenic fibers attached, or any combination of the above. The thrombogenic material may be attached to the device by any suitable means, including tying, weaving, wrapping, or attaching by a silicone or other acceptable adhesive.

Figure 4:
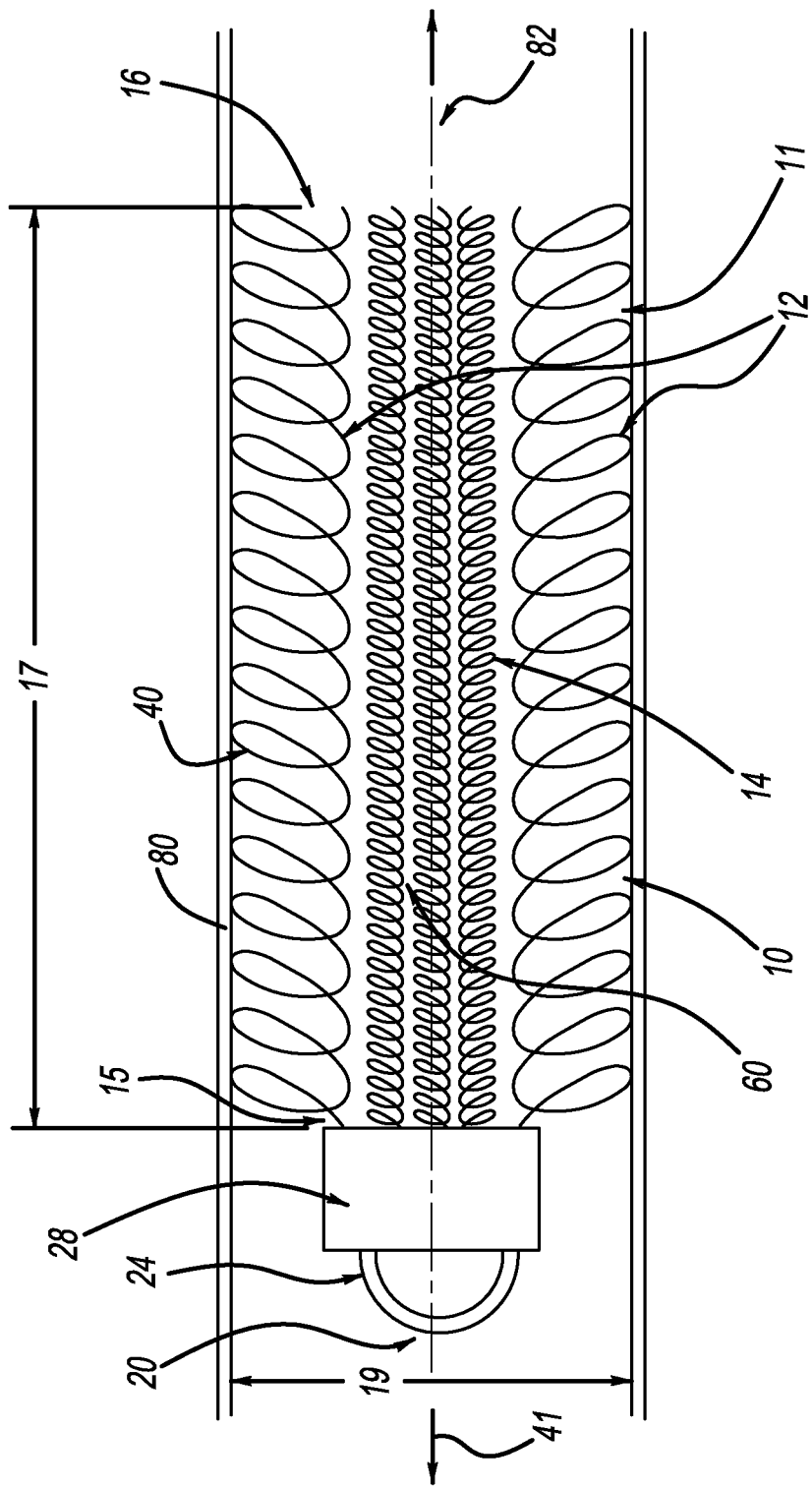
FIG. 4 is a side view of an occlusion device inside a delivery catheter in accordance with another embodiment of the present invention.

Referring now to FIG. 4, another embodiment of the device is shown. The device of FIG. 4 differs from the device of FIG. 1 in that there is no cap at the distal end 30. As a result, the distal ends of the outer coils 12 and the inner coils 14 are not enclosed.

Figure 5:
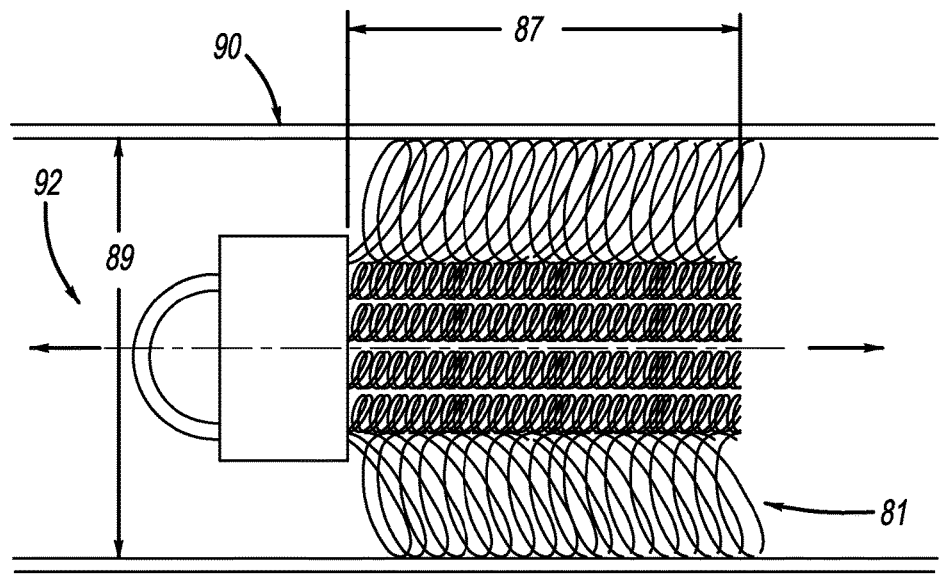
FIG. 5 is a side view of the occlusion device of FIG. 4 deployed within a body vessel.

FIG. 5 depicts the second configuration 81 of the device without a cap at distal end 30. As with the two-capped device of FIGS. 1A and 2, the device expands radially when deployed due to the springlike nature of the resilient outer coils 12. The softer inner coils 14 can be left unconstrained within the vessel lumen 92, or can be fastened together prior to insertion in the delivery catheter. Optionally, the inner coils 14 can be manipulated manually by the interventionalist using a hook or snare that accompanies the device in the delivery assembly. The inner coils 14 in particular can take on a "random" or "bunched" arrangement, which can provide a suitable configuration for occlusion of a vessel or cavity. The deployed configuration can have a less ordered configuration of inner coils 14 than the first configuration within the delivery apparatus.

Figure 6:
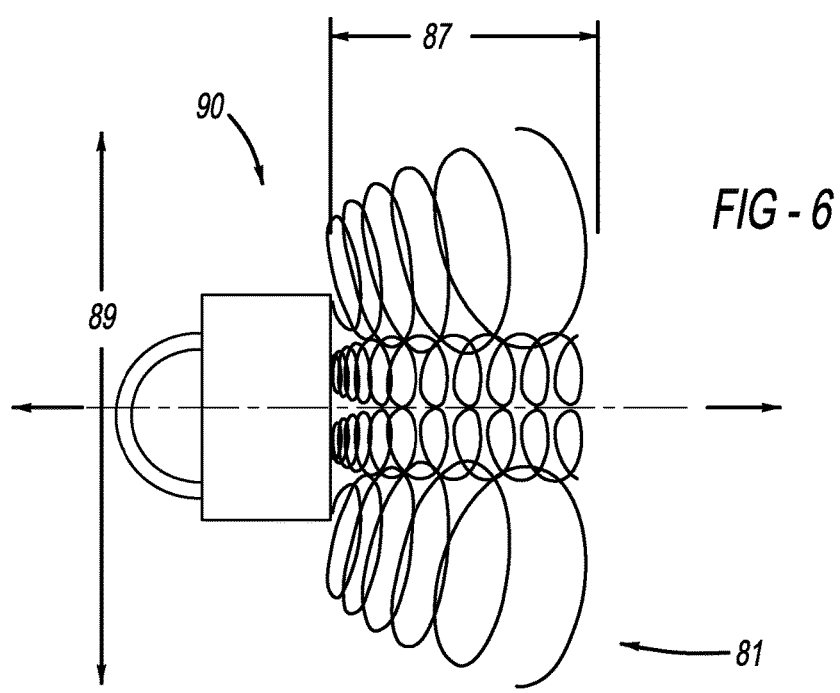
FIG. 6 is a side view of the occlusion device of FIG. 4 in an unconstrained configuration.

FIG. 6 is the third configuration 91 for the device with a free distal end 30. When not constrained by a delivery apparatus or a body vessel, along with no restraint imposed by a cap at the distal end 30, the device reverts to its state of lowest potential energy. In the embodiment depicted, this results in a spreading of the coils away from the longitudinal axis 41. In some embodiments, the distances between the coil windings may increase as the individual coils relax. In some embodiments this can result in a substantially conical shape for the device in the third configuration 91.

As with the two-cap embodiment of the device, a device having a single cap may also have some or all of its coils coated with a thrombogenic substance or have thrombogenic fibers attached thereto. In certain embodiments, the single-cap embodiment can be advantageous in situations where rapid deployment of the device are necessary, as the free distal end 30 of the device will provide nearly-instant contact with vessel walls when advanced out of the delivery apparatus and may additionally provide an additional force from the expansion of its free distal end in order to extricate the device from the delivery apparatus all the more quickly.

Figure 7A:
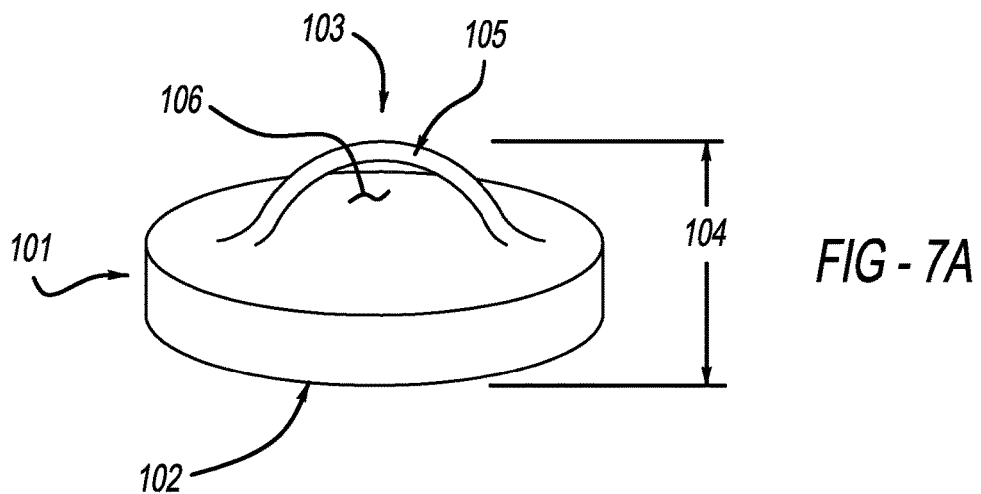
FIG. 7A-C are views of caps and retrieval portions in accordance with various embodiments of the invention.
Figure 7B:
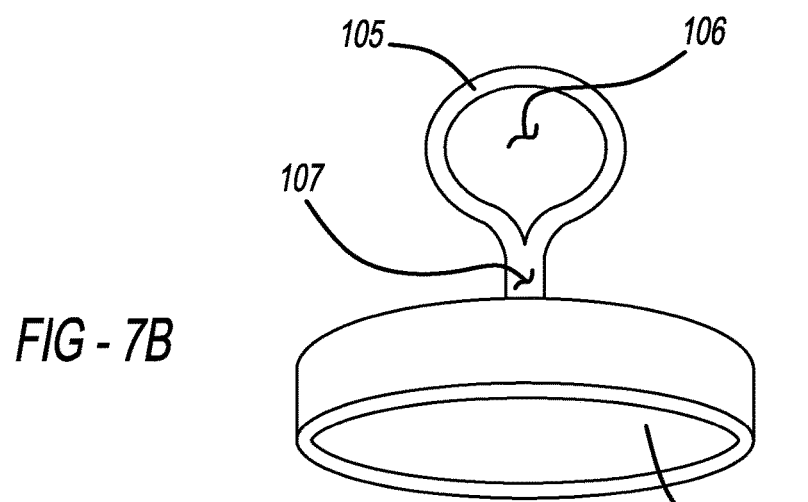
Figure 7C:
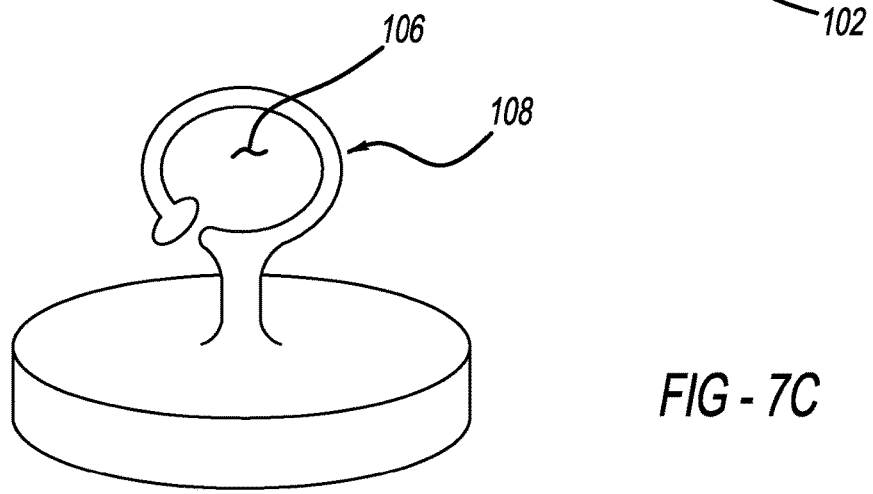

FIGS. 7A-7C depict various embodiments of a cap 101 that can be used in accordance with embodiments of the device. In one embodiment, the cap 101 has a cap lumen 102 that forms a portion for the insertion of ends of the outer coils 12, the inner coils 14, or both. The cap has a top end 103 which, when attached to the proximal end 20 or distal end 30 of a device, constitutes the most proximal or most distal surface, respectively, of the device as a whole.

The cap also optionally comprises a positioning member 105. In FIG. 7A, the positioning member is an engagement loop which defines a space 106 between the positioning member 105 and a portion of top end 103. The space 106 is a place where a delivery apparatus having a snare or a hook for deployment can engage the device as it is delivered to the body vessel or body cavity it is to occlude. The highest point of positioning member 105 to the bottom portion of the cap defines a cap height 104.

Many variations on cap structure can be used in accordance with the principles of this device. In FIG. 7B, the positioning member 105 is a closed loop set apart from the top surface of the cap by spacer 107. FIG. 7C shows another embodiment of a cap wherein the positioning member is a blunt-ended hook 108. The cap structure can be modified in order to accommodate the particular tools involved in delivery of the device.

One method of delivering the device includes introducing a delivery apparatus within the blood vessel 90 and providing the occlusion device 10 in its undeployed first configuration 11. A two-sheath configuration can be used to deliver the device. Such a configuration might include an inner sheath containing a tool for manipulating the device such as a pusher member optionally terminating in a hook or a snare to engage the proximal end 20 of the occlusion device 10. The device is also housed within the inner sheath, and the inner sheath is set within an outer sheath. The outer sheath extends at least to the distal end 30 of the occlusion device 10 to maintain the occlusion device 10 in the undeployed first configuration 11. This minimizes radial expansion of the device prior to arrival at the site to be occluded.

When the delivery system is properly positioned at a desired location within the body vessel or body cavity, the outer sheath can be withdrawn in a proximal direction to allow the distal end of the occlusion device 10 to move into the vessel lumen 92 and being to expand radially within the body vessel 90.

At this stage, the interventionalist can readily monitor the positioning of the occlusion device 10 using the intrinsic radiopacity of the coils of the device or, if they are made of a non radiopaque material, a radiopaque tag that has been incorporated into the device 10. If necessary, the device 10, which has not been fully deployed, can be withdrawn back into the outer sheath of the delivery assembly to allow repositioning.

Once the distal end 30 of the occlusion device 10 has been properly positioned, the outer sheath can be withdrawn further to allow radial expansion and occlusion. In the case of a one-cap embodiment of the invention, engagement of the distal portion of the device 10 with the vessel or cavity wall helps to avoid migration of the occlusion device 10 during deployment. This also initiates occlusion of the vessel as the entire diameter of the vessel should at this point be engaged.

After the device has been positioned appropriately, the inner sheath and the outer sheath are withdrawn so that the entirety of the occlusion device 10 is within the vessel lumen. A pusher member or other engagement device that can manipulate the device by cap 101 can be used if the removal of the sheaths is not sufficient to affect complete positioning and deployment of the device 10.

During deployment, contrast injection can be used to verify the position of the occlusion device 10. If adjustment is required, the device can be manipulated by engaging a cap member at positioning member 105.

While the above method describes a single method of deployment, a person of ordinary skill in the art will appreciate that other deployment methods are possible.

The embodiments of the present invention have many advantages. The occlusion device 10 provides a series of stiff outer coils 12 that help to maintain the overall shape of the device and also provide radial force to keep the device in place when deployed. The more pliant inner coils 14 provide a great amount of surface area for thrombi to collect. Moreover, any of the coils can be coated with a thrombogenic material or thrombogenic fibers to speed occlusion in the case of a blood vessel. If needed, the device can be made without a distal cap in order to provide nearly-instant contact with vessel walls during deployment and an extra force for thrusting the device out of the delivery catheter. Moreover, this combination of coils avoids an iterative process of adding coils until occlusion is achieved by providing a single-step deployment protocol.

As a person skilled in the art will readily appreciate, the above description is meant as an illustration of the implementation of the principles of this invention. This description is not intended to limit the scope or application of this invention in that the invention is susceptible to modification variation and change, without departing from the spirit of this invention, as defined in the following claims.

The invention claimed is:

1. An occlusion device for occlusion of a body vessel, the occlusion device having a longitudinal axis, the occlusion device comprising:
    a plurality of outer coiled elements, each outer coiled element having a first proximal end extending distally to a first distal end, each outer coiled element having a first diameter and a first length dimension, the first length dimension being substantially parallel to the longitudinal axis, the plurality of outer coiled elements defining a device body having a proximal device end extending distally to a distal device end and an interior device lumen disposed therethrough, the device body comprising a body outer surface disposed about the interior device lumen wherein each outer coiled element is disposed about the body outer surface, the device body including a device midpoint disposed substantially halfway between the proximal device end and the distal device end;
    a plurality of inner coiled elements disposed in the interior device lumen, each inner coiled element having a second proximal end extending distally to a second distal end, each inner coiled element having a second length dimension and a second diameter, the second diameter being less than the first diameter of any of the plurality of outer coiled elements; and
    a proximal cap disposed at the proximal device end, the proximal cap comprising a first interior portion and a first exterior portion, the first proximal ends of the outer coiled elements and the second proximal ends of the inner coiled elements being fixed within the first interior portion of the proximal cap.

2. The occlusion device of claim 1 wherein each outer coiled element further comprises a series of first coil loops, each first coil loop having a radius, each first coil loop being spaced substantially equidistant from the first coil loop proximal to and distal to it.

3. The occlusion device of claim 2 wherein the radius of each first coil loop is substantially equal to the radius of the first coil loop proximal to it.

4. The occlusion device of claim 2 wherein from the proximal device end to the device midpoint the radius of each first coil loop is larger than the radius of the first coil loop proximal to it, and from the device midpoint to the distal device end the radius of each first coil loop is smaller than the radius of the first coil loop proximal to it.

5. The occlusion device of claim 1 further having a constrained configuration wherein the device body has a constrained length and a constrained diameter and an unconstrained configuration wherein the device body has an unconstrained length and an unconstrained diameter, the constrained length being greater than the unconstrained length, the constrained diameter being smaller than the unconstrained diameter.

6. The occlusion device of claim 1 further comprising a distal cap disposed at the distal device end, the distal cap comprising a second interior portion and a second exterior portion, the first distal ends of the outer coiled elements and the second distal ends of the inner coiled elements being fixed within the second interior portion of the distal cap.

7. The occlusion device of claim 1 wherein the first exterior portion of the proximal cap further comprises a retrieval device engagement member.

8. The occlusion device of claim 7 wherein the retrieval device engagement member comprises an engagement loop.

9. The occlusion device of claim 1 wherein the outer coiled elements are made of a first material and the inner coiled elements are made of a second material, the first material having a greater stiffness than the second material.

10. The occlusion device of claim 9 wherein the first material is a metal alloy comprising nickel.

11. The occlusion device of claim 9 wherein the second material is platinum.

12. The occlusion device of claim 9 wherein the second material is palladium.

13. The occlusion device of claim 1 wherein the outer coiled elements have at least one portion comprising thrombogenic fibers.

14. The occlusion device of claim 13 wherein the thrombogenic fibers are made of a third material being selected from the group consisting of Dacron, polyester, and silk.

15. An occlusion device for occlusion of a body vessel, the occlusion device having a longitudinal axis, the occlusion device comprising:
    an outer coiled element having a first proximal end extending distally to a first distal end, the outer coiled element having a first diameter and a first length dimension, the first length dimension being substantially parallel to the longitudinal axis, the outer coiled element comprising a series of first coil loops, each first coil loop having a radius, each first coil loop being spaced substantially equidistant from the first coil loop proximal to and distal to it, the radius of each first coil loop being larger than that of the first coil loop proximal to it, the first coil loops defining a device body having a proximal device end extending distally to a distal device end and an interior device lumen disposed therethrough, the device body comprising a body outer surface disposed about the interior device lumen wherein each outer coiled element is disposed about the body outer surface;

a plurality of inner coiled elements disposed in the interior device lumen, each inner coiled element having a second proximal end extending distally to a second distal end, each inner coiled element having a second length dimension and a second diameter, the second diameter being less than the first diameter of the outer coiled element; and a proximal cap disposed at the proximal device end, the proximal cap comprising a first interior portion and a first exterior portion, the first proximal end of the outer coiled element and the second proximal ends of the inner coiled elements being fixed within the first interior portion of the proximal cap.

16. The occlusion device of claim 15 further having a constrained configuration wherein the device body has a constrained length and a constrained diameter and an unconstrained configuration wherein the device body has an unconstrained length and an unconstrained diameter, the constrained length being greater than the unconstrained length, the constrained diameter being smaller than the unconstrained diameter.

17. The occlusion device of claim 16 wherein the first exterior portion of the proximal cap further comprises a retrieval device engagement member.

18. The occlusion device of claim 17 wherein the outer coiled elements are made of a first material and the inner coiled elements are made of a second material, the first material having a greater stiffness than the second material.

19. The occlusion device of claim 15 wherein the outer coiled element includes at least one portion comprising thrombogenic fibers.

* * * * *